United States Patent [19]

Sievers et al.

[11] 4,251,233

[45] Feb. 17, 1981

[54] LIQUID HYDROCARBON-SOLUBLE RARE EARTH CHELATES PREPARED FROM THE NOVEL LIGAND 2,2,7-TRIMETHYL-3,5-OCTANEDIONE AND FUELS CONTAINING SAME

[75] Inventors: Robert E. Sievers; Thomas J. Wenzel, both of Boulder, Colo.

[73] Assignee: University Patents, Inc., Norwalk, Conn.

[21] Appl. No.: 17,459

[22] Filed: Mar. 5, 1979

[51] Int. Cl.$^3$ ............................................. C10L 1/18
[52] U.S. Cl. ................................. 44/68; 260/429 J; 260/429.2
[58] Field of Search .................. 260/429.2, 429 J; 44/68

[56] References Cited

U.S. PATENT DOCUMENTS

| | | | |
|---|---|---|---|
| 2,086,775 | 7/1937 | Lyons et al. | 44/68 |
| 2,151,432 | 3/1939 | Lyons et al. | 44/68 |
| 3,003,859 | 10/1961 | Irish et al. | 44/68 |
| 3,794,473 | 2/1974 | Eisentraut et al. | 44/68 |
| 3,946,057 | 3/1976 | Reedy | 260/429.2 |
| 4,036,605 | 7/1977 | Hartle | 44/68 |

FOREIGN PATENT DOCUMENTS 219409  8/1957  Australia ...................... 44/68

OTHER PUBLICATIONS

Seebach et al., "Synthesis . . . and Formation of Chiral 1,3-Diketones by Acylation", *Angew. Chem. Internat. Ed. Eng.*, 1972 11(2) 127–128.

*Primary Examiner*—Deborah L. Kyle

[57] ABSTRACT

Liquid hydrocarbon-soluble rare earth chelates prepared from the novel ligand 2,2,7-trimethyl-3,5-octanedione when dissolved in fuels such as gasoline and diesel oil prevent formation and/or effect removal of carbonaceous deposits during the combustion thereof. The use of fuels containing these chelates promotes more efficient operations of devices such as internal combustion engines in which the fuels are burned by minimizing or eliminating the accumulation of harmful carbonaceous materials in the combustion chambers and by preventing knocking and/or other undesirable performance characteristics.

11 Claims, No Drawings

LIQUID HYDROCARBON-SOLUBLE RARE EARTH CHELATES PREPARED FROM THE NOVEL LIGAND 2,2,7-TRIMETHYL-3,5-OCTANEDIONE AND FUELS CONTAINING SAME

This invention relates to the fields of acyclic ketones, metal chelating complexes prepared therefrom, and additives which influence the combustion of carbon-containing fuels, and more particularly, to beta-diketones and liquid hydrocarbon-soluble rare earth metal beta-diketonates, liquid hydrocarbon motor fuels containing such chelates and methods for operating internal combustion engines employing such fuels.

Lead alkyls, most notably tetraethyl lead, have been widely used as antiknock additives for gasoline since the early 1920's. In recent years, however, steps have been taken to eventually eliminate the use of lead alkyls as fuel additives on environmental grounds. At present, resort to the use of larger quantities of aromatic hydrocarbon components is made in order to improve the octane rating of motor fuels. Large amounts of aromatics in gasoline cause undesirable exhaust emissions and increased exposure to benzene which has been linked to leukemia. In addition to this environmental penalty, it has been estimated that the removal of lead alkyls from gasoline reduces the amount of gasoline recoverable from a barrel of crude oil by about 6 percent. Accordingly, there exists a great need for a lead-free antiknock agent which is environmentally acceptable and does not accelerate the depletion of dwindling petroleum reserves.

A major contributing cause of engine knock is known to be due to the accumulation of carbonaceous deposits within the combustion chambers. The deposits reduce the volume of each combustion chamber resulting in an increase in engine compression ratio. The increased engine compression in turn causes a proportional increase in the octane number requirement of the engine. This increase, however, accounts for only about 10 to 20% of the octane requirement increase (ORI), the balance of the increase being due to other factors occasioned by the existence of the deposits. It has been speculated that the deposits catalyze the combustion process with a resulting tendency to cause detonation and/or preignition. It has also been thought that the deposits may exert an insulating effect which decreases the rate of heat transfer through the cylinder walls. This causes an increase in combustion temperature, a condition which makes the engine more prone to knock.

Numerous substances possessing antiknock activity have been proposed as replacements for tetraethyl lead. Methylcyclopentadienylmanganese tricarbonyl (MMT) which has recently been developed as an antiknock additive reportedly causes the catalysts of exhaust converters to malfunction and its use has been forbidden in lead free gasolines. The article "Volatile Metal Complexes" by Robert E. Sievers and Jean E. Sadlowski, Science, July 21, 1978, Volume 201, pp. 217-223, discloses a number of liquid hydrocarbon-soluble rare earth metal beta-diketonate chelates useful as fuel additives including the holmium and erbium complexes of the homologous beta-diketone, 2,2,6,6-tetramethyl-3,5-heptanedione (H(thd)). Recently, it has been observed that rare earth chelates prepared from H(thd) promote the degradation of liquid hydrocarbon fuels to such an extent as to be virtually useless as practical fuel additives. Other metal beta-diketonates and related compounds which have been proposed for use in motor fuels are described in U.S. Pat. Nos. 2,086,775; 2,151,432; 3,003,859; 3,794,473; and, 4,036,605; and, United Kingdom patent specifications Nos. 287,192; 502,171; and, 525,890. Additional metal chelates which, however, are not identified as useful fuel additives are described in U.S. Pat. Nos. 3,014,939; 3,119,851; 3,580,938; 3,634,477; 3,647,832; and, 4,003,937. Beta-diketones and/or methods for their preparation are described in U.S. Pat. Nos. 2,395,800; 2,417,381; and, 2,432,499. In view of the experience with the rare earth metal complexes derived from H(thd) supra, there would be no basis for supposing that any rare earth metal complexes derived from homologues of H(thd) much less other beta-diketones, would have a substantially reduced tendency to degrade hydrocarbon fuels.

It has now been discovered that liquid hydrocarbon-soluble rare earth metal chelating complexes derived from the novel beta di-ketone 2,2,7-trimethyl-3,5-octanedione (H(tod)) intermittently or continuously present in fuels such as gasoline, diesel oil, benzene, kerosene, etc., and blends thereof, prevent formation and/or effect removal of carbonaceous deposits during the combustion of the fuels. When added to motor fuels, the rare earth metal chelates of this invention minimize or eliminate the accumulation of carbonaceous deposits in the combustion chambers of internal combustion engines in which the fuels are employed reducing the ORI and suppressing the tendency of the engines to knock. Unlike the rare earth metal chelates derived from H(thd), the present chelates demonstrate entirely acceptable levels of stability in liquid hydrocarbon fuels. Rare earth compounds are known to be far less toxic than the lead salts produced by combustion of tetraethyl lead and unlike tetraethyl lead and MMT, are unlikely to poison noble metal catalysts such as are used in automotive exhaust converters. As such, the rare earth metal chelates of this invention are ideally suitable fuel additives and are even advantageously employed in fuels which already contain an antiknock additive such as tetraethyl lead. The precise mechanism by which the rare earth metal (tod) chelates inhibit or eliminate the formation of carbonaceous deposits is not known with any certainty. It is thought that during the combustion process, the chelates release the rare earth metals in the form of extremely fine particles of oxide which in turn catalyze the low temperature combustion of carbonaceous materials present in the combustion chambers facilitating their removal therefrom. This explanation is given by way of suggesting a possible mechanism by which the chelates herein operate and is not intended to limit the invention in any way.

The process for preparing H(tod) which possess the structure

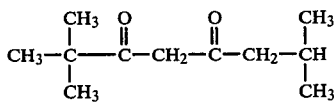

from inexpensive and readily obtainable raw materials represents another important advantage of the present invention. The rare earth metal chelating complexes of H(tod) can be prepared by any suitable method, e.g., by reaction with rare earth metal halides in the presence of strong base.

In accordance with this invention, H(tod) is prepared by reacting methylisobutyl ketone (MIBK) which has the formula

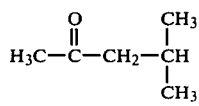

with an ester of the formula

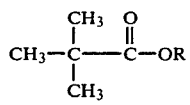

in which R is an unsubstituted hydrocarbyl group or a hydrocarbyl group containing one or more non-interfering substituents, and an alkali metal hydride of the formula MeH in which Me is an alkali metal, to provide H(tod), a light-yellow liquid which has a boiling point of 55° C. at 0.1 mm hg. The compound exists in both the ketonic and enolic forms.

The reaction of MIBK, ester and alkali metal hydride to form H(tod) involves two separate reactions which proceed as follows:

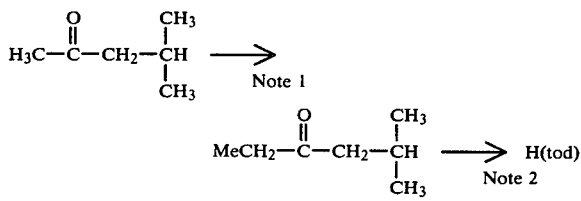

1 MeH, preferably at elevated temperature
2 React with aforementioned ester

It is, of course, within the scope of this invention to bring the MIBK, hydride and ester into simultaneous contact to form H(tod) which is preferred, or to separately react the MIBK with the hydride and thereafter react the resulting organoalkali metal intermediate with the ester to form H(tod).

The term "non-interfering substituents" as applied to the R moiety of the ester reactant herein contemplates those groups which do not significantly prevent or impede the progress of the above reaction. The ester is conveniently prepared by any of the known and conventional ester synthesis techniques and is advantageously obtained from the reaction of neopentanoic acid which has the formula

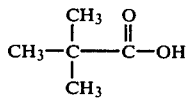

with an alcohol ROH in which R has the above meaning, in the presence of an esterification catalyst under conditions well known in the art. Suitable alcohols include methanol, ethanol, n-propanol, isopropanol, n-butanol, sec.-butanol, tert.-butanol, 2-ethyl-1-butanol, n-pentanol, n-hexanol, 2-butoxyethanol, 2-methoxyethanol, 3-methoxy-1-butanol, 2-chloroethanol, and the like. Ethanol is especially preferred as the esterifying alcohol, the resulting ester being ethyl pivalate. In one embodiment of the process herein, ethyl pivalate is combined with a mineral oil dispersion of sodium hydride in a suitable solvent such as toluene and following the heating of these reactants, MIBK is added to the reaction medium under stirring whereupon H(tod) forms. Standard recovery procedures can be used if it is desired to separate the H(tod) from unreacted materials, by-products, solvent, etc.

The rare earth metal (tod) chelates can be represented by the general formula:

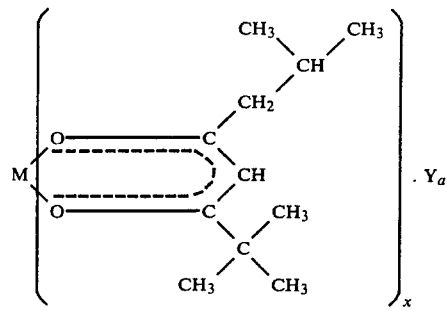

in which M is a rare earth element or a mixture thereof, Y is water or an organic compound containing a donor group, a is 0 to 4 and x is 1 to 4. The rare earths include the following elements: lanthanum (La), cerium (Ce) praeseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Lu), scandium (Sc), yttrium (Y). For the sake of economy, it is preferred to employ a mixture of rare earth compounds derived from a naturally occurring rare earth ore. Such an ore will typically have the composition shown in the following table:

| Typical Rare Earth Ore | |
|---|---|
| Rare Earth Oxide | Weight % |
| $La_2O_3$ | 24 |
| $CeO_2$ | 48 |
| $Pr_6O_{11}$ | 5 |
| $Nd_2O_3$ | 17 |
| $Sm_2O_3$ | 3 |
| $Gd_2O_3$ | 2 |
| $Y_2O_3$ | 0.2 |
| Other rare earth oxides | 0.8 |

The preparation of the rare earth metal (tod) chelates herein can be conducted by a procedure analogous to that disclosed in U.S. Pat. No. 3,794,473 which is incorporated by reference herein. A methanolic solution of one or several rare earth metal halides is added to a methanolic solution of H(tod) and alkali metal hydroxide, ammonium hydroxide or other strong base is added under constant agitation to provide the chelate or chelate mixture which can be recovered employing standard techniques.

The rare earth metal (tod) chelates are readily soluble in most organic solvents. For the preparation of the additive concentrates, the chelates herein can be dissolved in amounts of from 1 up to about 10 weight percent of solvent or even higher. Suitable organic solvents are: hydrocarbon solvents, for example, petroleum fractions such as naphtha, kerosene and furnace oils; aromatic hydrocarbons such as benzene, toluene, and xylene; paraffinic hydrocarbons such as hexane, octane and iso-octane. Alcohols such as methanol, ethanol, propanol, and butanol can also be used. Other solvents which can be employed are ketones and esters such as acetone, methyl ethyl ketone, ethyl acetate, butyl acetate, and the like. The solvent employed should, of course, be selected with regard to the possible beneficial or adverse effects it may have. Thus, the solvent should burn without leaving an objectionable residue and should be non-corrosive to metals. A particularly suitable additive concentrate contains about 5 weight percent rare earth metal (tod) chelate in xylene.

The rare earth metal (tod) chelates of this invention can be effectively utilized as fuel additives to obtain the beneficial effectiveness of the rare earth components in minimizing ORI, reducing surface ignition, imparting wear reduction effectiveness, improving octane ratings, alleviating spark plug fouling and other problems associated with internal combustion engines of both the spark and compression ignition types. The chelates can be dissolved and intimately mixed with liquid hydrocarbon fuels for internal combustion engines to impart the aforesaid beneficial effects. Similarly, the chelates herein can be added to bunker oils and furnace oils for improvement of the combustion properties of these fuels. When added to gasoline and furnace oils, for example, the chelates can generally be used at a level of from about 0.001 to about 50 millimoles per gallon to provide effective results.

The rare earth metal (tod) chelates can be incorporated into the fuels in any suitable manner. Thus, they can be added as such to gasoline or they can be added in the form of concentrates, supra. If desired, the chelates of this invention can be used with conventional gasoline additives including other antiknock agents, particularly tetraethyl lead, upper cylinder lubricants, corrosion and oxidation inhibitors, ignition control agents, metal deactivators, dehazing agents, anti-rust agents, deicing agents, dyes and the like. The gasoline fuels to which addition of the chelates herein is contemplated includes substantially all grades of gasoline presently employed in internal combustion engines.

The following examples are illustrative of the invention.

EXAMPLE I

This example illustrates the preparation of the ligand H(tod) and the chelate mixture Ce(tod)$_4$-Ln(tod)$_3$

A. Preparation of Ethyl Pivalate

Absolute ethanol (1035 ml) was added to 306 grams of neopentanoic acid (Exxon) in a flask fitted with a heating mantle and a reflux condenser. To this mixture was slowly added 65 ml of concentrated sulfuric acid (Mallinckrodt). The mixture was then heated under reflux for three hours. Heating was discontinued and the hot mixture was extracted with 4 liters of a 10% sodium carbonate solution. The organic layer which separated was collected and dried overnight with magnesium sulfate. It was then filtered and purified by distillation at atmospheric pressure. A low heat was first applied in order to collect a fraction at a temperature of 73° C. consisting principally of ethanol. When the head temperature began to drop, the heat was raised and a second fraction, consisting of ethyl pivalate was collected from 108°–111° C. This pure ethyl pivalate (yield about 77%) was then dried over magnesium sulfate.

B. Preparation of H(tod)

A three-neck round-bottom flask was fitted with a reflux condenser with an attached drying tube containing calcium chloride, a dropping funnel, and a glass tube connected by Tygon tubing to a tank of nitrogen gas. During the reaction, the mixture was continually stirred by a magnetic stirring apparatus. Toluene (350 ml) which had been dried over Linde Molecular Sieve 4A, was then added to the flask. A gentle flow of nitrogen, passed through a trap containing Linde Molecular Sieve 13X, was used to continually sweep out the system. Sodium hydride (67.2 grams of a 50% dispersion in mineral oil) was then added to the toluene, followed by 106.5 ml of ethyl pivalate. The MIBK (88 ml which had been dried over Linde Molecular Sieve 3A) was placed in the dropping funnel and, prior to addition, the mixture in the flask was heated to 96° C. in a boiling water bath. The addition was done dropwise over the course of three hours. Heat was continued for an additional half hour, after which the reaction was left stirring under nitrogen overnight. At this point, the mixture was a greenish-yellow color and no additional toluene was needed to keep the mixture stirring.

The next day the flask was packed in an ice bath and 260 ml of an 18% hydrochloric acid solution was slowly added. During the neutralization, the nitrogen flow was left on and stirring was done as vigorously as possible. The two resulting layers were filtered by suction filtration. The organic layer was then collected, and the toluene was removed by rotary evaporation. The resulting organic residue which was made up largely of H(tod) (about 81% yield) was of suitable purity to be used directly in the synthesis of the rare earth metal chelates.

C. Preparation of Ce(tod)$_4$-Ln(tod)$_3$

Since the final chelate additive was to consist of approximately 50 weight percent Ce(tod)$_4$ and 50 weight percent Ln(tod)$_3$ (where Ln is a mixture of principally La, Pr and Nd), one mole of rare earth chloride mixture (approximate molecular weight of the hydrated chloride is 356) was needed for 3.5 moles of H(tod) (356 g of hydrated rare earth chloride is needed for 644 g of H(tod)). The correct amount of the rare earth chloride mixture was then powdered and dissolved in methanol at a ratio of 1000 ml of methanol for 75 g of the rare earth chloride mixture. The H(tod) in methanol was added and 4 M sodium hydroxide was slowly added as the mixture was vigorously stirred. The pH was brought up to a final value of eight by addition of aqueous NaOH. The methanol solution was then poured off, leaving behind a thick red oily residue consisting of rare earth tod. This residue was then dissolved in a mixture of hexanes and filtered by suction through a medium porosity sintered glass funnel. Hexane (500 ml) and distilled water (1000 ml) were added to the methanol solution which was extracted by vigorous shaking. The hexane layer was collected and filtered. The hexane solutions were combined and evaporation of the hexane yielded a dark red oil. Crystallization was achieved by dissolving approximately 100 g of the oil in 300 ml of hexane, adding this solution to 1000 ml of 95% ethanol, and letting the entire solution sit overnight. The plate-like crystals were collected, dissolved in hexane, and filtered through a medium pore glass funnel. The hexane was removed with a rotary evaporator, leaving a fine, dark red powder consisting of a 50/50 weight percent of Ce(tod)$_4$ and Ln(tod)$_3$ (about 65% yield).

EXAMPLE II

This example illustrates the preparation of H(tod) employing a purification procedure and the preparation of another mixture of rare earth metal (tod) chelates.

A. Preparation of H(tod)

One equivalent of ethyl pivalate (prepared as in Example I) was placed in a round bottomed flask with 2 equivalents of NaH (dispersion in mineral oil) and enough toluene to keep the reaction mixture fluid. The reaction mixture was heated using a water bath, and 1 equivalent of MIBK was added dropwise to the reaction mixture over a period of 3–4 hours. Toluene was added as necessary to keep the slurry fluid enough to stir. The reaction mixture was heated and stirred for a total period of 4 hours. The mixture was then allowed to stand overnight with a stream of dry N$_2$ passing over it. The reaction mixture was then neutralized with an excess of 18% HCl. The mixture (both aqueous and organic layers) was filtered and the solid and the aqueous layer were discarded. The solvent was removed from the organic layer with a rotary evaporator. The remaining relatively nonvolatile organics contained the H(tod) ligand. The ligand was purified by placing the organic mixture over an acid solution, then adding a 4 M NaOH solution while stirring vigorously. As the NaOH was added, Na(tod) formed as a solid while the salt of neopentanoic acid and other impurities went into the aqueous layer. The H(tod) ligand was recovered by placing the solid Na(tod) in an acid solution and collecting the organic layer that formed on the surface.

B. Preparation of Rare Earth Metal (tod) Chelates

A mixture of all the hydrated rare earth chlorides was employed. The percent of each metal present was governed by that amount found in the oxide ore. In samples of roasted leachates from bastnasite ore from the Molycorp (Union Oil Co.) mine at Mountain Pass, Calif., the basic composition was found to be 50% cerium, which will form Ce(tod)$_4$ chelate, and 50% other lanthanides which form chelates of the formula Ln(tod)$_3$, where Ln represents elements with atomic numbers from 57 to 71, inclusive, and yttrium.

To 162 grams of the rare earth chloride mixture dissolved in 1000 ml of absolute methanol, was added 304 grams of H(tod) previously dissolved in 300 ml of absolute methanol. The mixture was vigorously stirred while 4 M sodium hydroxide was slowly added to bring the pH up to 6.8. The entire contents of the beaker were transferred to a separatory funnel and extracted with 1000 ml of a mixture of hexanes. The aqueous layer was then extracted again with 500 ml of fresh hexanes. The hexane layers were combined and filtered through a medium porosity glass funnel. The hexane was then removed with a rotary evaporator. Crystallization of the rare earth metal (tod) chelate mixture which appeared in the form of a dark red oil was achieved by dissolving approximately 100 grams of the oil in 300 ml of hexanes. This hexane mixture was then added to 1000 ml of vigorously stirred 95% ethanol. This mixture was allowed to stand overnight. Long needle-like crystals formed which were collected by suction filtration. One hundred grams of the crystals were then dissolved in 300 ml of a mixture of hexanes and the hexanes were then removed with a rotary evaporator. After thorough drying, a dark red powder remained, and this powder had the composition consisting principally of a mixture of La(tod)$_3$, Ce(tod)$_4$, Pr(tod)$_3$, Nd(tod)$_3$, and lesser percentages of other rare earth metal (tod) chelates. The chelates exhibited mass spectra characteristic of the formulas indicated. The mixture of rare earth metal (tod) chelates was highly soluble in gasoline and was volatile, two highly desirable properties which make them useful as fuel additives. Because they are synthesized from inexpensive MIBK they are much less expensive than the complexes of dipivaloylmethane H(thd)) of the *Science* publication, supra, which is made from the much more expensive ketone, pinacalone.

EXAMPLE III

The ability of the mixture of rare earth metal (tod) chelates of Example II to effectively remove accumulated carbonaceous deposits was demonstrated in a single-cylinder old lawn mower engine. Before the test, the spark plug in the engine was heavily coated with dark carbonaceous deposit. Removal of the head showed the cylinder to contain a great deal of a black gummy material. A fuel mixture was prepared consisting of enough rare earth metal (tod) chelate mixture in unleaded gasoline to contain 2 grams of metal per gallon of gasoline. The engine was started and allowed to operate at full throttle until all the fuel was consumed. After one quart of the mixture had been burned, the spark plug was again removed and checked. The black material which has previously been present was completely removed. The plug appeared at this time to be clean except for a thin, yellow oxide coating. Inspection of the cylinder showed that the deposit which remained was less gummy and much more rigid and flaky. In some areas of the cylinder the deposit had been completely removed.

After operating the motor to consume a second quart of gasoline with the new additives, the spark plug appeared relatively clean. The deposit in the cylinder had the same oxide coating as the spark plug, and the cleanliness of the combustion chamber appeared improved over that seen on first inspection of the engine. In view of the results of the test, it is apparent that the use of the rare earth metal (tod) chelates as fuel additives does alter combustion deposits and reduces pre-ignition, dieseling, and octane requirement increase (ORI).

EXAMPLE IV

The resistance to degradation of a sample of gasoline containing the 50/50 weight percent mixture of Ce(tod)$_4$-Ln(tod)$_3$ chelates of Example II (Sample A) was compared with that of a sample of the same gasoline containing an identical amount of a 50/50 weight percent mixture of Ce(thd)$_4$-Ln(thd)$_3$ (Sample B). The test procedure was in accordance with ASTM D 525-Standard Test Method for Oxidation Stability of Gasoline (Induction Period Method) which determines the stability of gasoline under accelerated oxidation conditions. The induction period is used as an indication of the tendency of gasoline to form gum in storage. 50±1 ml of the sample of chelate-containing gasoline to be tested was placed in an oxidation bomb initially filled at 15° to 25° C. with oxygen at 100 psi and then heated to a temperature between 98° and 102° C. The temperature was maintained within this range by immersion of the bomb in a water bath. The temperature to the nearest 0.1° C. was recorded at regular intervals during the test. The test was continued until a point was reached which was preceded by a pressure drop of exactly 2 psi in 15 minutes and succeeded by a drop of not less than 2 psi in 15 minutes (the "break point"). Whereas Sample A did not reach the break point even after 24 hours, Sample B had reached this point between 15 minutes and 4 hours, and indication that the fuel had degraded to a considerable extent. This test demonstrates the superior stability of gasolines containing rare earth metal (tod) chelate additives compared to gasolines containing the related rare earth metal (thd) chelates of the prior art.

EXAMPLE V 10 g of $Ce(NO_3)_3.6H_2O$ was dissolved in 30 ml of methanol. To this was added a solution of 17 g of H(tod) in 50 ml of methanol. The solution was stirred and 4 M NaOH was slowly added until the pH had reached a value of 7. During the addition of the base, the solution gradually turned a dark red color and precipitate starts to settle out at a pH value of about 6.4. The entire mixture is then added to a separatory funnel. Distilled water (100 ml) and hexane (75 ml) was added and the Ce(tod)$_4$ was extracted into the hexane layer. This layer was collected, filtered through a medium porosity sintered glass funnel and the hexane was removed with a rotary evaporator. The dark red crystals of Ce(tod)$_4$ (MP=134°-136° C.) were collected. The yield was essentially quantitative.

When using H(tod) which comes directly from the synthesis of H(tod) and is not pure, evaporation of the hexane in the last step will yield a dark red oil. In this case, crystallization was achieved by dissolving the oil in about 100 ml of hexanes and adding the solution to 400 ml of 95% ethanol.

The mixture was allowed to stand overnight and the crystals of Ce(tod)$_4$ which had formed were collected. These were then dissolved in hexanes and filtered through a medium porosity sintered glass funnel. The hexanes were removed on a rotary evaporator leaving dark red crystals of Ce(tod)$_4$.

EXAMPLE IV

The synthesis used for the different rare earth tod tris chelates is identical and is described here for the Pr(tod)$_3$ compound.

10 g of $Pr(NO_3)_3.6H_2O$ was dissolved in 100 ml of methanol. To this was added 12.7 g of H(tod) in 25 ml of methanol. The solution was stirred as the pH was brought up to a value of 8 by the slow addition of 4 M NaOH. An oily precipitate starts to settle out of the solution at a pH of about 6.4. The entire mixture was then transferred to a separatory funnel. Distilled water (100 ml) and hexanes (75 ml) were added and the Pr(tod)$_3$ was extracted into the hexane layer. This layer was then collected and filtered through a medium porosity sintered glass funnel. The hexane solution was subsequently added to 400 ml of 95% ethanol and allowed to stand overnight. The crystals which had formed were collected, redissolved in hexanes and filtered again through a medium porosity funnel. The hexanes were removed with a rotary evaporator leaving a fine green powder, Pr(tod)$_3$ (MP=219°-223° C.).

La(tod)$_3$ and Nd(tod)$_3$ were synthesized in addition to Pr(tod)$_3$ using procedures identical to that described above. The Nd(tod)$_3$ compound has a pale blue color and melts in the range 228°-230° C. The La(tod)$_3$ is white and melts under the range 172°-176° C.

Mass spectral data on the pure compounds is as reported below.

| | m/e | Relative abundance | Assignments |
|---|---|---|---|
| Ce(tod)$_4$ | 57 | 37.5 | t-butyl |
| | 127 | 45.3 | tod-t-butyl |
| | 504 | 10.9 | |
| | 506 | 84.4 | m-2 tod |
| | 507 | 31.3 | |
| | 508 | 23.4 | |
| | 509 | 10.9 | |
| | 689 | 100.0 | m-tod |
| | 690 | 73.4 | |
| | 691 | 40.6 | |
| | 692 | 12.5 | |
| | 872 | 12.5 | molec. ion |
| La(tod)$_3$ | 85 | 78.6 | tod + CO |
| | 127 | 66.7 | tod-t-butyl |
| | 128 | 42.9 | |
| | 183 | 64.3 | tod |
| | 505 | 100.0 | m-tod |
| | 506 | 28.6 | |
| | 631 | 31.0 | m-t-butyl |
| | 632 | 11.9 | |
| | 688 | 16.7 | molec. ion |
| Pr(tod)$_3$ | 57 | 12.3 | t-butyl |
| | 127 | 26.3 | tod-t-butyl |
| | 507 | 100.0 | m-tod |
| | 508 | 26.3 | |
| | 633 | 33.3 | m-t-butyl |
| | 634 | 10.5 | |
| | 690 | 22.8 | molec. ion |
| Nd(tod)$_3$ | 57 | 33.3 | t-butyl |
| | 127 | 41.7 | tod-t-butyl |
| | 508 | 100.0 | m-tod |
| | 509 | 70.8 | |
| | 510 | 91.7 | |
| | 511 | 55.8 | |
| | 512 | 75.0 | |
| | 513 | 18.3 | |
| | 514 | 25.8 | |
| | 516 | 22.5 | |
| | 634 | 32.5 | m-t-butyl |
| | 635 | 25.0 | |
| | 636 | 35.8 | |
| | 637 | 23.3 | |
| | 638 | 27.5 | |
| | 691 | 20.8 | molec. ion |
| | 692 | 16.7 | |
| | 693 | 20.8 | |
| | 694 | 13.3 | |
| | 695 | 15.0 | |

All four compounds exhibit molecular ions in the spectra. In addition, for all compounds, the major peak in the spectrum corresponds to the loss of one tod ligand.

The following infrared data were observed for the pure compounds La(tod)$_3$, Pr(tod)$_3$, Nd(tod)$_3$ and Ce(tod)$_4$. Spectra of all compounds were obtained using KBr pellets with a Perkin Elmer MOdel 467 Grating Infrared instrument. The spectrum of Ce(tod)$_4$ was poorly resolved, perhaps because it contained several strong absorption bands.

| Pr(tod)$_3$ | Nd(tod)$_3$ | La(tod)$_3$ | | Ce(tod)$_4$ |
|---|---|---|---|---|
| 2942s | 2949s | 2947s | | 2947m |
| 2902sh | 2865m | 2862m | | 2860sh |
| 2862m | 1576s | 1493–1583s | (broad) | 1562s |
| 1568s | 1505s | 1402s | (broad) | 1502s |
| 1517s | 1408s | 1358s | | 1403m |
| 1397s | 1357s | 1332sh | | 1217w |
| 1360s | 1340sh | 1282m | | 1154w |
| 1339sh | 1289m | 1215s | | 975w |
| 1290m | 1222s | 1154s | | 770w |
| 1223m | 1158s | 966m | | |
| 1161m | 970m | 886m | | |
| 965w | 890m | 768m | | |

-continued

| Pr(tod)₃ | Nd(tod)₃ | La(tod)₃ | Ce(tod)₄ |
|---|---|---|---|
| 892w | 772m | 605m | |
| 775w | 615m | 471w | |
| 610w | 474w | | |
| 476w | | | |

We claim:

1. A liquid hydrocarbon-soluble rare earth metal chelate in which the ligand is 2,2,7-trimethyl-3,5-octanedione, and mixtures thereof.

2. The rare earth metal chelate or chelate mixture of claim 1 in which the rare earth metal is selected from the group consisting of lanthanum, cerium, praseodymium, neodymium, samarium, europium, gadolinium, terbium, dysprosium, holmium, erbium, thulium, ytterbium, lutetium, scandium and yttrium.

3. A concentrate comprising an organic solvent containing at least 1% by weight of a rare earth metal chelate or chelate mixture of claim 1.

4. A liquid hydrocarbon fuel containing a combustion deposit modifying amount of a rare earth metal chelate or chelate mixture of claim 1.

5. The liquid hydrocarbon fuel of claim 4 wherein the fuel is gasoline.

6. The liquid hydrocarbon fuel of claim 5 wherein the gasoline contains from about 0.001 to about 50 millimoles rare earth metal chelate or chelate mixture per gallon.

7. A liquid hydrocarbon-soluble rare earth metal chelate or chelate mixture consisting essentially of a complex of the general formula;

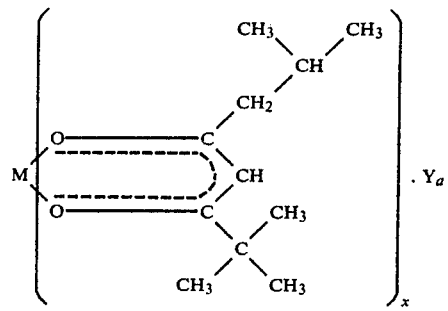

in which M is a rare earth element or a mixture thereof, Y is water or an organic compound containing a donor group, a is 0 to 4 and x is 1 to 4.

8. The rare earth metal chelate or chelate mixture of claim 7 in which the rare earth metal is selected from the group consisting of lanthanum, cerium, praseodymium, neodymium, samarium, europium, gadolinium, terbium, dysprosium, holmium, erbium, thulium, ytterbium, lutetium, scandium and yttrium.

9. A concentrate comprising an organic solvent containing at least 1% by weight of rare earth metal chelate or chelate mixture of claim 7.

10. A liquid hydrocarbon fuel containing a combustion deposit modifying amount of a rare earth metal chelate or chelate mixture of claim 7.

11. The liquid hydrocarbon fuel of claim 10 wherein the fuel is gasoline.

* * * * *